(12) United States Patent
Amano

(10) Patent No.: US 6,616,937 B2
(45) Date of Patent: Sep. 9, 2003

(54) COSMETIC COMPOSITION CONTAINING A DISTILLATE OF A GREEN PLANT JUICE AND A PROCESS FOR PREPARING THE SAME

(76) Inventor: Takahiko Amano, 97 San Bernadino, Ventura, CA (US) 93004

( * ) Notice: Subject to any disclaimer, the term of this patent is extended or adjusted under 35 U.S.C. 154(b) by 0 days.

(21) Appl. No.: 10/146,963

(22) Filed: May 17, 2002

(65) Prior Publication Data

US 2002/0168391 A1 Nov. 14, 2002

Related U.S. Application Data

(63) Continuation of application No. 09/563,921, filed on May 4, 2000, now abandoned.

(51) Int. Cl.$^7$ .......................... A61K 7/42; A61K 35/78; A61K 9/14; A61K 9/16

(52) U.S. Cl. ....................... 424/401; 424/488; 424/489; 424/195.1

(58) Field of Search ................................. 424/401, 488, 424/499, 195.1

(56) References Cited

FOREIGN PATENT DOCUMENTS

GB          1 358 052      *  6/1974

* cited by examiner

*Primary Examiner*—Shelley A. Dodson
(74) *Attorney, Agent, or Firm*—Sherman & Shalloway

(57) ABSTRACT

An improved cosmetic composition comprises at least one cosmetically effective ingredient and water, where at least a potion of the water has been replaced by a distillate of a green plant juice. The distillate is obtained from a green plant juice, produced by squeezing green plants, by evaporation of the green plant juice to cause a concentration increase of the green plant juice.

8 Claims, No Drawings

COSMETIC COMPOSITION CONTAINING A DISTILLATE OF A GREEN PLANT JUICE AND A PROCESS FOR PREPARING THE SAME

CROSS REFERENCE TO RELATED APPLICATION

This application is a continuation of application Ser. No. 09/563,921, filed May 4, 2000 now abn.

BACKGROUND OF THE INVENTION

1. Field of the Invention

The present invention relates to cosmetic compositions which normally contain purified or distilled water wherein the water has been at least partially replaced by a distillate of a green plant juice. More particularly, the present invention is directed to cosmetic compositions containing at least one cosmetically effective ingredient and a distillate of a green plant juice; and methods of producing the same.

2. Description of the Prior Art

Fresh raw edible green plants are very important foodstuffs for the maintenance of health, but they involve problems concerning edibility, e.g., in that they are tough and hard to digest. In order to solve these problems, various foodstuffs comprising green plant juice squeezed from a fresh raw edible green plant or its dry powder have been proposed in the prior art.

In the preparation of such dry powders, a large amount of liquid is removed from the green plant juice and then discarded as a waste material.

The present invention provides a use for this by-product liquid.

BRIEF SUMMARY OF THE INVENTION

It is an object of the present invention to utilize an otherwise discarded by-product of the manufacture of a dry powder of green plant juice.

It is a further object of the present invention to provide a cosmetic composition having reduced requirements for preservative materials.

It is a still further object of the present invention to provide a process for producing a cosmetic composition having reduced requirements for preservative materials.

These objects of the invention, and others that will become apparent upon reading the disclosure of this invention, are achieved by the provision of an improved cosmetic composition comprising at least one cosmetically effective ingredient and water, wherein the improvement is the replacement of at least a portion of the water by a distillate of a green plant juice.

Additionally, the present invention provides an improved process for producing a cosmetic composition comprising mixing at least one cosmetically effective ingredient and water, wherein the improvement is the replacement of at least a portion of the water by a distillate of a green plant juice.

BRIEF DESCRIPTION OF THE DRAWINGS

FIG. 1 is a graph illustrating the antioxidant activity of the distillate of green plant juice as tested in Example 2.

DETAILED DESCRIPTION OF THE INVENTION

The presently contemplated distillate of a green plant juice is obtained as a by-product of the production of dry powder of green plant juice squeezed from a fresh raw edible green plant.

In this production process, the leaves and/or stems, preferably leaves and stems, of young green plants are harvested; the harvested materials are washed with water; the washed materials are squeezed to collect a green plant juice; the green plant juice is concentrated (producing the distillate of a green plant juice used in this invention and a concentrate); the concentrate is spray-dried into a powder; and the powder is granulated and packed into jars.

The green plants which are used as starting materials in the present invention are preferably edible green plants and these include not only cultivated edible plants having green leaves or stems, but also edible wild grasses and herbs having green leaves and stems; plants having green leaves and stems which are not usually eaten, such as fruit, vegetables, root crops, cereals and fruit trees; green edible algae; and the like. Specific examples thereof include green leaves of barley and wheat, spinach, lettuce, cabbage, Chinese cabbage, Japanese cabbage, cucumber, bitter melon, pimento, carrot leaves, radish leaves, parsley, celery, "ashitaba" (*Angelica keiskei* (Miq.) koidz.), comfrey leaves, green leaves of grasses, (e.g., alfalfa, clover and kale), striped bamboo leaves, persimmon leaves, pine needles, spirulina, chlorella, "wakame seaweed" (*Undaria pinnatifida* (Harvey) Suringar) and green laver. These plants may be used alone or in combination of two or more.

Among the foregoing green plants, cereals such as barley, wheat, rye, oats, pearl barley, corn, millet and Italian ryegrass are preferred. Of these, barley (in particular, its leaves and stems before maturation) is most preferred.

It is desirable to treat these green plants while they are as fresh as possible. Where stored plants are used, it is preferable that they have been subjected to proper measures for the prevention of discoloration and deterioration, such as inert gas storage, cold storage, deaerated and dehydrated storage, or treatment with sulfur dioxide or a sulfite salt. A green plant used as the starting material is thoroughly washed to remove all of the matter adhering thereto, preferably such washing is effected using room temperature water (with no detergents being involved); sterilized with a germicide (e.g., hypochlorous acid), as desired; further washed thoroughly with water; and, optionally, cut to pieces of appropriate size. When cut to pieces, the plant may be soaked in a dilute aqueous solution of sodium chloride (e.g., a 0.1–2% aqueous solution of sodium chloride) and cut therein. Moreover, at any stage of this pretreatment, the plant may be subjected to a blanching treatment at a temperature of 100° C. to 140° C. under atmospheric pressure (or under sub-atmospheric or super-atmospheric pressure in some cases) for about 2 to 10 seconds and then cooled rapidly. This treatment serves to inactivate enzymes which may cause undesirable discoloration or deterioration of green plants (e.g., chlorophyllase, peroxidases and polyphenol oxidase).

After the green plant is pre-treated in the above-described manner, juice is squeezed therefrom. The squeezing can readily be carried out according to any conventionally known method, for example, by the combined use of a mechanical disintegration means (such as a mixer or juicer) and a solid-liquid separation means (such as a centrifuge or a filter apparatus). Water may be added to the green plant material prior to the squeezing in order to facilitate handling of the green plant material. After the squeezing, the pH of the resulting green juice may be adjusted to a pH of 6.2 to 9.5, preferably 6.5 to 8.5, more preferably, about 6.5 to 7.5, by use of a base.

Bases which can be used for the above-described pH adjustment include hydroxides, carbonates and bicarbonates of alkali metals and alkaline earth metals, such as sodium hydroxide, calcium hydroxide, magnesium hydroxide, sodium carbonate, potassium carbonate, calcium carbonate and sodium bicarbonate; ammonium hydroxide; glutamic acid salts such as calcium glutamate; and kelp extract.

At any stage following the separation of the green juice and preceding the drying treatment, the green plant juice may be subjected to a flash heating treatment for decomposing or inactivating undesirable enzymes which will participate in discoloration or deterioration, and also destroying bacteria which may be present therein. This treatment may be carried out under atmospheric, sub-atmospheric or super-atmospheric pressure, using a heating temperature of 90° C. to 150° C. and a treating time of about 180 to 2 seconds. After such a treatment, it is desirable to cool the juice rapidly, particularly to a temperature of 10° C. or below.

As described previously, the green plant juice having undergone the pH adjustment is spray-dried or freeze-dried, preferably spray-dried, as soon as possible. The spray-drying or freeze-drying may be carried out according to any conventionally known method.

For example, in the case of spray drying, hot spray drying using hot air at about 120° C. to 200° C., preferably 140° C. to 170° C., or cold spray drying using air dried with a suitable desiccant, e.g., lithium chloride, may be employed. In the case of freeze drying, treating conditions such as drying plate temperature of 40° C. to 50° C. and a vacuum of the order of 1.0 to 0.01 mmHg are usually employed.

The concentration of the green plant juice (i.e. solids content) used in the drying step should be in the range of about 1.5 to 30% and preferably as high as possible within those limits. In order to concentrate the green juice to this end, a continuous thin-film concentrator or a vacuum distillation apparatus or the like may be used, preferably, a centrifugal-flow, thin-film vacuum evaporator wherein, most preferably, the atmospheric pressure is reduced so as to allow evaporation of water at a temperature of about 40° C. It is the distillate of the green plant juice produced in this concentration step, a by-product normally disposed of as waste, that is utilized in the present invention.

In the course of the above-described procedures, various means, such as the replacement of air by an inert gas (e.g., nitrogen or argon), the inclusion of an oxygen absorber (e.g., glucose oxidase), maintenance at low temperatures and protection from light, may be used, alone or in any combination, to prevent the green plant juice from being discolored or deteriorated during transfer and storage preceding the drying step.

The distillate of the green plant juice produced in the concentration step may be utilized in the formulation of cosmetic compositions because of its strong antioxidant and antiseptic properties.

Cosmetic compositions are preparations applied to the surface of the body for the purpose of enhancing its appearance. These compositions can be make-up preparations, applied to bring about temporary effects, lasting only so long as the preparations remain on the body surface, or treatment preparations, which effect no immediately noticeable change but which, after repeated use, are expected to have a beautifying effect.

The present distillate of the green plant juice finds particular use in cosmetic compositions containing water, i.e. as a substitute for at least a portion of the pure water or distilled water normally compounded in such compositions. Generally, at least about 25% of the water should be replaced, in order to take advantage of the antioxidant and antiseptic properties of the distillate of the green plant juice, preferably at least about 50%, more preferably at least about 75%, and most preferably 100%.

The cosmetic compositions of the present invention may be skin care products such as lotions, creams, cleansers, etc. The compositions of the invention may be emulsions of liquid or semi-liquid consistency of the milk type, obtained by dispersion of an oil phase in an aqueous phase or vice versa; or suspensions or emulsions of soft consistency of the cream type.

All oils used in the production of cosmetic compositions are suited for use in the compositions of the present invention. There may be mentioned hydrocarbons such as mineral oils, petrolatum and squalane; animal and vegetable triglycerides such as almond oil, peanut oil, wheat germ oil, linseed oil, jojoba oil, oil of apricot pits, oil of walnuts, oil of palm nuts, oil of pistachio nuts, oil of sesame seeds, oil of rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil; hydroxy-substituted $C_8$–$C_{50}$ unsaturated fatty acids and esters thereof; $C_1$–$C_{24}$ esters of $C_8$–$C_{30}$ saturated fatty acids such as isopropyl myristate, cetyl palmitate and octyl-dodecylmyristate (Wickenol 142); beeswax; saturated and unsaturated fatty alcohols such as behenyl alcohol and cetyl alcohol; fatty sorbitan esters; lanolin and lanolin derivatives; $C_1$–$C_{24}$ esters of dimer and trimer acids such as diisopropyl dimerate, diisostearylmalate, diisostearyldimerate and triisostearyltrimerate; and silicones such as water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof.

While the distillate of the green plant juice of the present invention has antioxidant properties which may allow the preparation of compositions without the addition of other antioxidants, it is possible to use standard antioxidants such as t-butyl hydroquinone, butylated hydroxytoluene and α-tocopherol and its derivatives in the cosmetic compositions of the present invention, preferably, in amounts less than would normally be utilized.

Similarly, while the distillate of the green plant juice of the present invention has antiseptic properties, which may allow the preparation of compositions without the addition of other preservatives, it is possible to use standard preservatives such as methyl, ethyl, propyl, butyl and isobutyl p-hydroxybenzoate (parabems), 2-phenoxyethanol, sorbic acid, potassium sorbate, hexamidine diisothionate, imidazolidinylurea (Germall 115) or preservatives marketed under the names Kathon and Tridssan.

A wide variety of optional ingredients such as non-occlusive moisturizers, humectants, gelling agents, neutralizing agents, perfumes, coloring agents and surfactants can be added to the presently contemplated cosmetic compositions.

A humectant may be present in an amount of from about 0.1% to about 20%, preferably from about 1% to about 10% and especially from about 2% to about 5% by weight of the total composition. Suitable humectants include sorbitol, propylene glycol, butylene glycol, hexylene glycol, ethoxylated glucose derivatives, hexanetriol, glycerine, water-soluble polyglycerylmethacrylate lubricants (e.g., compositions available under the trademark Lubrajel) and panthenols (e.g. D-panthenol).

A hydrophilic gelling agent may be present in an amount of from about 0.01% to about 10%, preferably from about 0.02% to about 2% and especially from about 0.02% to about 0.5% by weight of the total composition. Suitable hydrophilic gelling agents include cellulose ethers (e.g., hydroxyethyl cellulose, hydroxypropylmethyl cellulose), polyvinylalcohol, guar gum, hydroxypropyl guar gum and xantham gum, as well as the acrylic acid/ethyl acrylate copolymers and the carboxyvinyl polymers sold under the trademark Carbopol.

Neutralizing agents, suitable for use in neutralizing acidic group containing hydrophilic gelling agents, include sodium hydroxide, potassium hydroxide, ammonium hydroxide, monoethanolamine, diethanolamine and triethanolamine.

Other optional materials include keratolytic agents such as salicylic acid; proteins and polypeptides and derivatives thereof; soluble or colloidally-soluble moisturizing agents such as hylaronic acid and starch-grafted sodium polyacrylates; coloring agents; perfumes and perfume solubilizers; surfactants/emulsifiers such as fatty alcohol ethoxylates and ethoxylated polyol fatty acid esters; and pigments which can be organic or inorganic and which include materials having a low color or lustre, such as matte finishing agents, and also light scattering agents.

The compositions of the present invention may be prepared by any conventional technique for preparing a cosmetic composition by merely substituting the distillate of green plant juice for the water normally incorporated into the composition.

The following examples are illustrative and are not intended to limit the invention in any way.

EXAMPLE 1

Young green leaves of barley (i.e., leaves and stems of barley before maturation) are thoroughly washed with water, disintegrated with a mixer, and squeezed. A green juice is obtained by filtering off fibrous residue. The green juice is vacuum distilled (pressure=about 55 mm Hg) in a centrifugal-flow-thin-film vacuum evaporator (EVAPOR®, Model No. CEP-305, made by Okawara Mfg. Co., Ltd. Shizuoka, Japan), the juice being poured on to the conical evaporating surface, rotating at 300 to 500 RPM, to form a thin film of about 0.1 mm thickness, with a residence time on the evaporating surface of only about one second. The outside of the rotating conical evaporating surface is jacketed and heated evenly by steam (inlet temp.=130° C., outlet temp.=80° C.). A tube at the edge of the rotating evaporating surface collects concentrate.

The distillate is a clear watery liquid with a very slightly greenish color and a refreshing grassy odor.

An analysis was conducted according to an internal standard method as described by L. S. Ettre in *The Practice of Gas Chromatography*, Ettre, L. S., Zlatkis, A., Eds., Interscience Publishers: New York, 1967, p. 402. A Hewlett-Packard model HP5890 Series II gas chromatograph equipped with a 60 m×0.25 mm i.d. ($d_f$=1 μm) DB-WAX bonded-phase fused silica capillary column (J&W Scientific, Folsom, Calif.) was used and interfaced to an HP5791A mass selective detector for mass spectral identification of the components. The linear velocity of the helium carrier gas was 30 cm/sec, the oven temperature was programmed from 50° C. to 200° C. at 3° C./min and held for 40 minutes, and the ionization voltage for mass spectral identification was 70 eV.

An analysis is shown in Table A.

TABLE A

| No. | R. TIME | R. Index | CONC | COMPOUNDS |
|---|---|---|---|---|
| 1 | 2.762 | 0 | 0.01 | |
| 2 | 2.860 | 0 | 0.00 | 3-methyl-1-butene |
| 3 | 2.908 | 0 | 0.00 | |
| 4 | 2.962 | 0 | 0.01 | |
| 5 | 3.060 | 600 | 0.00 | |
| 6 | 3.317 | 702 | 0.01 | acetaldehyde |
| 7 | 3.950 | 792 | 0.18 | propanal |
| 8 | 4.291 | 820 | 0.01 | |
| 9 | 4.486 | 833 | 0.01 | |
| 10 | 4.603 | 841 | 0.00 | |
| 11 | 5.458 | 900 | 0.02 | |
| 12 | 5.560 | 904 | 0.02 | butanal |
| 13 | 6.362 | 933 | 0.01 | |
| 14 | 6.511 | 939 | 0.00 | |
| 15 | 6.701 | 945 | 0.08 | 2-ethylfuran |
| 16 | 7.022 | 957 | 0.00 | |
| 17 | 7.428 | 972 | 0.54 | 3-pentanone |
| 18 | 7.548 | 977 | 0.01 | |
| 19 | 7.638 | 980 | 0.01 | |
| 20 | 7.824 | 987 | 0.02 | 2-methyl-3-buten-2-one |
| 21 | 8.101 | 997 | 0.02 | |
| 22 | 8.557 | 1009 | 0.01 | 2-methyl-2-butanol |
| 23 | 8.992 | 1019 | 7.42 | 1-penten-3-one |
| 24 | 9.280 | 1025 | 0.00 | |
| 25 | 9.430 | 1029 | 0.00 | |
| 26 | 9.573 | 1032 | 0.02 | (E)-2-butenal |
| 27 | 9.780 | 1037 | 0.00 | |
| 28 | 9.850 | 1039 | 0.00 | |
| 29 | 10.023 | 1043 | 0.00 | |
| 30 | 10.423 | 1052 | 0.03 | 2,3-pentanedione |
| 31 | 10.751 | 1059 | 0.00 | |
| 32 | 11.279 | 1072 | 0.01 | |
| 33 | 11.465 | 1076 | 0.42 | hexanal |
| 34 | 11.749 | 1083 | 0.01 | |
| 35 | 12.594 | 1102 | 0.02 | |
| 36 | 12.850 | 1106 | 0.00 | |
| 37 | 13.013 | 1109 | 0.04 | 3-pentanol |
| 38 | | | t | 2-pentanol |
| 39 | 13.769 | 1123 | '0.82 | (E)-2-pentenal |
| 40 | 14.287 | 1132 | 0.10 | (E)-3-hexenal |
| 41 | 14.585 | 1137 | 0.22 | (Z)-3-hexenal |
| 42 | 16.226 | 1166 | 22.12 | 1-penten-3-ol |
| 43 | 16.540 | 1172 | 0.00 | |
| 44 | 16.939 | 1179 | 0.02 | 3-penten-2-ol |
| 45 | 17.565 | 1190 | 0.01 | |
| 46 | 17.930 | 1196 | 0.21 | (Z)-2-hexenal |
| 47 | 19.341 | 1219 | 14.55 | (E)-2-hexenal |
| 48 | 20.369 | 1235 | 0.05 | |
| 49 | 21.431 | 1252 | 0.17 | pentanol |
| 50 | 22.560 | 1269 | 0.01 | |
| 51 | 23.141 | 1279 | 0.08 | 3-hydroxybutan-2-one |
| 52 | 23.720 | 1288 | 0.01 | |
| 53 | 24.040 | 1293 | 0.00 | |
| 54 | 24.280 | 1296 | 0.00 | |
| 55 | 25.430 | 1314 | 0.42 | (E)-2-pentenol |
| 56 | 26.564 | 1332 | 34.67 | (Z)-2-pentenol |
| 57 | 27.160 | 1341 | 0.07 | |
| 58 | 27.480 | 1346 | 0.05 | |
| 59 | 28.176 | 1356 | 0.37 | hexanol |
| 60 | 28.176 | 1356 | 0.05 | 2-hydroxypentan-3-one |
| 61 | 28.757 | 1365 | 0.15 | (E)-3-hexenol |
| 62 | | | | |
| 63 | 30.263 | 1388 | 4.27 | (Z)-3-hexanol |
| 64 | 30.708 | 1395 | 0.14 | (E,E)-2,4-hexadienal |
| 65 | 31.200 | 1403 | 0.02 | |
| 66 | 31.578 | 1408 | 0.82 | (E)-2-hexanol |
| 67 | 32.330 | 1420 | 0.03 | (E)-2-octenal |
| 68 | 34.345 | 1451 | 0.03 | 1-octen-3-ol |
| 69 | 34.776 | 1458 | 0.21 | (E,Z)-2,4-heptadienal |
| 70 | 36.537 | 1485 | 0.11 | (E,E)-2,4-heptadienal |
| 71 | 36.537 | 1485 | 0.01 | (Z)-1,5-octadien-3-ol |
| 72 | 36.920 | 1491 | 0.01 | 2-ethylhexanol |
| 73 | 38.418 | 1515 | 0.18 | |
| 74 | 38.920 | 1523 | 0.17 | |
| 75 | | | t | propanoic acid |

TABLE A-continued

| No. | R. TIME | R. Index | CONC | COMPOUNDS |
|---|---|---|---|---|
| 76 | 39.669 | 1535 | 0.12 | 4-oxohexanal |
| 77 | 40.000 | 1540 | 0.06 | |
| 78 | 41.251 | 1560 | 0.56 | octanol |
| 79 | 42.080 | 1574 | 0.02 | |
| 80 | 42.386 | 1579 | 0.04 | (E,Z)-2,6-nonadienal |
| 81 | 42.897 | 1587 | 0.19 | |
| 82 | 43.389 | 1595 | 0.12 | 2-hydroxy-2,6,6-trimethylcyclohexanone |
| 83 | 43.800 | 1601 | 0.02 | |
| 84 | 44.215 | 1608 | 0.39 | |
| 85 | 44.720 | 1617 | 0.09 | beta-cyclocitral |
| 86 | 45.445 | 1629 | 0.12 | |
| 87 | 46.160 | 1641 | 0.03 | 3-hydroxyoctan-2-one |
| 88 | 46.649 | 1649 | 0.28 | |
| 89 | 47.640 | 1666 | 0.00 | |
| 90 | 48.123 | 1674 | 0.07 | 5-methyl-2(5H)-furanone |
| 91 | 49.006 | 1689 | 1.62 | |
| 92 | 49.923 | 1704 | 0.43 | |
| 93 | 51.000 | 1723 | 0.00 | |
| 94 | 51.440 | 1731 | 0.02 | |
| 95 | 51.920 | 1739 | 0.01 | |
| 96 | 52.533 | 1750 | 0.38 | 5-ethyl-2(5H)-furanone (T) |
| 97 | 52.799 | 1755 | 0.14 | |
| 98 | 53.314 | 1764 | 0.24 | |
| 99 | 54.303 | 1781 | 0.04 | |
| 100 | 54.678 | 1788 | 0.14 | |
| 101 | 55.197 | 1797 | 0.03 | |
| 102 | 55.921 | 1810 | 0.10 | |
| 103 | 56.440 | 1819 | 0.06 | |
| 104 | 57.130 | 1832 | 0.13 | |
| 105 | 57.517 | 1839 | 0.10 | |
| 106 | 58.040 | 1849 | 0.03 | hexanoic acid |
| 107 | 58.640 | 1860 | 0.00 | |
| 108 | 58.910 | 1864 | 0.04 | |
| 109 | 59.375 | 1873 | 0.05 | |
| 110 | 59.375 | 1873 | 0.11 | |
| 111 | 59.960 | 1884 | 0.01 | (E,E,E)-2,4,6-nonatrienal |
| 112 | 60.400 | 1892 | 0.02 | |
| 113 | 60.734 | 1898 | 0.02 | |
| 114 | 61.250 | 1908 | 0.09 | phenylethyl alcohol |
| 115 | 61.720 | 1917 | 0.06 | |
| 116 | 62.414 | 1930 | 0.26 | |
| 117 | 62.829 | 1938 | 0.15 | beta-ionone |
| 118 | 63.429 | 1949 | 0.07 | |
| 119 | 63.884 | 1958 | 0.08 | |
| 120 | 64.246 | 1965 | 0.61 | |
| 121 | 64.906 | 1978 | 0.40 | |
| 122 | 65.312 | 1985 | 0.15 | 5,6-epoxy-beta-ionone |
| 123 | 65.920 | 1997 | 0.24 | |
| 124 | 66.895 | 2016 | 0.07 | |
| 125 | 67.461 | 2028 | 0.17 | |
| 126 | 68.800 | 2055 | 0.02 | |
| 127 | 69.135 | 2061 | 0.04 | |
| 128 | 69.480 | 2068 | 0.01 | |
| 129 | 70.035 | 2079 | 0.03 | |
| 130 | 70.413 | 2087 | 0.06 | |
| 131 | 70.966 | 2098 | 0.04 | 2,6-di-tert-butyl-4-hydroxy-4-methyl-2,5-cyclohexadlen-1-one (T) |
| 132 | 71.600 | 2111 | 0.29 | |
| 133 | 72.179 | 2123 | 0.07 | |
| 134 | 72.763 | 2135 | 0.05 | |
| 135 | 73.245 | 2145 | 0.04 | |
| 136 | 74.000 | 2161 | 0.03 | |
| 137 | 74.400 | 2169 | 0.02 | |
| 138 | 75.257 | 2187 | 0.40 | |
| 139 | 75.610 | 2195 | 0.14 | |
| 140 | 76.782 | 2220 | 0.09 | |
| 141 | 77.497 | 2235 | 0.01 | |
| 142 | 77.920 | 2244 | 0.01 | |
| 143 | 78.342 | 2254 | 0.04 | |
| 144 | 78.778 | 2263 | 0.03 | |
| 145 | 79.347 | 2275 | 0.02 | |
| 146 | 79.680 | 2283 | 0.01 | |
| 147 | 80.026 | 2290 | 0.02 | |
| 148 | 81.920 | 2331 | 0.03 | dihydroactinidiolide |
| 149 | 81.920 | 2331 | 0.03 | |
| 150 | 82.664 | 2347 | 0.04 | |
| 151 | 83.417 | 2363 | 0.01 | diethyl phthalate |
| 152 | 84.629 | 2389 | 0.02 | |
| 153 | 85.118 | 2400 | 0.04 | tetracosane |
| 154 | 85.587 | 2408 | 0.07 | |
| 155 | 86.787 | 2429 | 0.03 | |
| 156 | 87.360 | 2439 | 0.01 | |
| 157 | 87.677 | 2445 | 0.05 | |
| 158 | 88.980 | 2468 | 0.02 | |
| 159 | 90.141 | 2489 | 0.05 | |
| 160 | 91.346 | 2508 | 0.02 | pentacosane |
| 161 | 92.293 | 2521 | 0.03 | phytyl acetate |
| 162 | 93.018 | 2531 | 0.02 | diisobutyl phthalate |
| 163 | 93.491 | 2538 | 0.01 | |
| 164 | 93.791 | 2542 | 0.01 | |
| 165 | 94.411 | 2551 | 0.01 | vanillin |
| 166 | 94.960 | 2559 | 0.01 | |
| 167 | 95.497 | 2566 | 0.01 | |
| 168 | 95.987 | 2573 | 0.01 | |
| 169 | 96.586 | 2581 | 0.01 | |
| 170 | 97.234 | 2590 | 0.10 | octadecanol |
| 171 | 97.880 | 2599 | 0.01 | hexacosane |
| 172 | 98.820 | 2610 | 0.07 | phytol |
| 173 | 100.251 | 2625 | 0.01 | 4-hydroxy-3-methoxyacetophenone |
| 174 | 101.071 | 2634 | 0.03 | |
| 175 | 102.299 | 2647 | 0.05 | |
| 176 | 103.240 | 2657 | 0.01 | |
| 177 | 105.148 | 2677 | 0.01 | |
| 178 | 105.790 | 2684 | 0.04 | |
| 179 | 106.463 | 2691 | 0.15 | dibutyl phthalate |
| 180 | 107.278 | 2700 | 0.01 | heptacosane |
| 181 | 109.078 | 2714 | 0.01 | |
| 182 | 114.139 | 2755 | 0.02 | |
| 183 | 118.800 | 2793 | 0.17 | bis(2-ethylhexyl) adipate |

EXAMPLE 2

250 ml of the distillate produced by the technique of Example 1 is extracted with 50 ml of dichloromethane using a liquid-liquid continuous extractor for 6 hours. The solvent is separated from the extract by using a rotary evaporator and further condensation is achieved under a purified nitrogen stream.

The extract is examined for antioxidative activity using an aldehyde/acid oxidation system. The method used is based on the auto-oxidation of aldehydes to carboxylic acids with active oxygen species such as hydroxy radical as discussed in *Autoxidation of various organic substances*, Horner, L., *Autoxidation and Antioxidants*, Lundberg, W. O., Ed., John Wiley & Sons, New York, 1961, pp. 197–202. The results, illustrated in FIG. 1, show that the extract inhibited oxidation of hexanol more than two weeks at the level of 50 ppm. This activity is almost equal to that of the well-known antioxidant, α-tocopherol.

A gas chromatogram of the extract shows more than 100 peaks, suggesting that the distillate contains many volatile chemicals some of which possess a potent antioxidant activity.

EXAMPLE 3

The distillate produced by the technique of Example 1 is passed through a 0.45 μm membrane filter to remove any barley juice residues.

Apples are peeled and immersed in regular tap water, filtered distillate or tap water containing salt for five minutes. The apples are then taken out and allowed to sit for 1 hour, whereupon their color is determined. The results are set forth in Table 1.

TABLE 1

| IMMERSION LIQUID | COLOR |
|---|---|
| Tap Water | 80% of the surface becomes brown or tan |
| Filtered Distillate | less than 5% of the surface becomes brown |
| Tap Water Containing Salt | less than 5% of the surface becomes brown |

EXAMPLE 4

Cut tulips are kept in tap water or the filtered distillate as in Example 3. The water and the filtered distillate are changed every other day. The result is shown in Table 2.

TABLE 2

| Liquid | Number of Days That Tulips Lasted |
|---|---|
| Tap Water | 5 |
| Filtered Distillate | 10 |

The tulips in filtered distillate last longer and are in better condition than those in tap water.

EXAMPLE 5

Two facial toners are prepared as set forth in Table 3.

TABLE 3

| | TONER | |
|---|---|---|
| INGREDIENT | A [1] | B |
| Butylene glycol | 60 g | 60 g |
| Sorbitol | 20 g | 20 g |
| Glycerin | 20 g | 20 g |
| Methylparaben | 0.6 g | 0.3 g |
| Phenoxyethanol | 0.5 g | 0.5 g |
| Sodium citrate | 0.1 g | 0.1 g |
| Butylparaben | 0.1 g | 0.05 g |
| Propylparaben | 0.1 g | 0.05 g |
| Citric acid | 0.02 g | 0.02 g |
| Distilled H$_2$O | balance | — |
| Filtered Distillate (Ex. 3) | — | balance |
| Total | 1,000 g | 1,000 g |

[1] - commercial product in Japan 18 ml. of toner A, 18 ml of toner B and 18 ml of a toner having the same formulation as toner A except for being devoid of preservatives are each inoculated with 2 ml of Staphylococcus aureus solution (Staphylococcus aureus in sterile diluent (pepton, lecithin, distilled water) at a concentration between $1\times10^6$ and $1\times10^7$) to make sample solutions A, B and C, respectively. Sample A, B and C are allowed to stand at room temperature and sampled at day 0, day 1, day 3, day 7, day 14 and day 21. Each time 1 ml of solution is taken and general bacteria plate count tests are performed. In the plate count tests, 1 ml. of sample solution and 20 ml of media are placed in a Petri dish, cultivated at 36° C. for 48 hours, and the number of colonies reported. Serial dilutions, such as $\frac{1}{10}$, $\frac{1}{100}$, $\frac{1}{1000}$, etc., are done if the colonies number more than 200 and the test procedures are repeated. The results are set forth in Table 4.

TABLE 4

| | SAMPLE | | |
|---|---|---|---|
| | A | B | C |
| Day 0 | $2.7 \times 10^5$ | $1.5 \times 10^5$ | $1.5 \times 10^5$ |
| Day 1 | 6.8 | 5.5 | $2.5 \times 10^4$ |
| Day 3 | 0 | 0.5 | $5.9 \times 10^7$ |
| Day 7 | 0 | 0 | $3.3 \times 10^7$ |
| Day 14 | 0 | 0 | $4.9 \times 10^7$ |
| Day 21 | 0 | 0 | $2.4 \times 10^7$ |

Samples A and B have similar antibacterial activities. Therefore, filtered distillate may be used in a cosmetic product to reduce the required amount of preservatives.

EXAMPLE 6

A toner having the following composition is prepared using the filtered distillate as in Example 3.

| | |
|---|---|
| 95% Ethanol | 100 g |
| Methyl p-hydroxybenzoate | 0.05 g |
| Perfume | 0.5 g |
| Colorant | 0.005 g |
| Filtered distillate | Balance |
| | 1,000 g |

This toner is used everyday after washing the face in the morning and before sleeping to examine the effect on spots and freckles. Evaluation was effected by comparing spots and freckles before and after a 6-week application period. The results obtained on a panel of 20 women are shown in Table 5.

TABLE 5

| EFFECT | COLOR[1] | BOUNDARY[2] |
|---|---|---|
| Effective | 5 | 7 |
| Slightly effective | 7 | 8 |
| No effect | 8 | 5 |

[1] - Color of spots and freckles
Dark Brown  No effect
Pale Brown  Slightly effective
Almost none  Effective

[2]—Boundary Between Snot or Freckle and Other Regular Skin Areas
Boundary apparent   No effect
Boundary unclear   Slightly effective
Boundary almost undiscernible   Effective

What is claimed is:

1. In a cosmetic composition comprising at least one cosmetically effective ingredient and water, the improvement comprising replacing at least a portion of said water with a liquid by-product of a green plant juice, wherein said liquid by-product exhibits antioxidant and antiseptic properties and comprises a normally discarded residue obtained from the concentration of green plant juice.

2. The cosmetic composition according to claim 1, wherein said green plant is an edible green plant.

3. The cosmetic composition according to claim 2, wherein said edible green plant is a cereal.

4. The cosmetic composition according to claim 3, wherein said cereal is barley.

5. In a process for producing a cosmetic composition comprising mixing at least one cosmetically effective ingredient and water, the improvement comprising replacing at least a portion of said water with a liquid by-product of a green plant juice obtained as a normally discarded residue from a process for concentrating green plant juice prior to drying said green plant juice to a powder, wherein said liquid by-product exhibits antioxidant and antiseptic properties.

6. The process according to claim 5, wherein said green plant is an edible green plant.

7. The process according to claim 6, wherein said edible green plant is a cereal.

8. The process according to claim 7, wherein said cereal is barley.

* * * * *